(12) United States Patent
Foster et al.

(10) Patent No.: US 9,820,939 B2
(45) Date of Patent: Nov. 21, 2017

(54) ANTIVIRAL COMPOSITIONS

(71) Applicants: Alison J. Foster, Liverpool (GB); James Long, Liverpool (GB); Steven P. Rannard, Liverpool (GB); Dong Wang, Liverpool (GB); David J. Duncalf, Liverpool (GB); Andrew Owen, Liverpool (GB)

(72) Inventors: Alison J. Foster, Liverpool (GB); James Long, Liverpool (GB); Steven P. Rannard, Liverpool (GB); Dong Wang, Liverpool (GB); David J. Duncalf, Liverpool (GB); Andrew Owen, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

(21) Appl. No.: 14/862,875

(22) Filed: Sep. 23, 2015

(65) Prior Publication Data

US 2016/0008281 A1 Jan. 14, 2016

Related U.S. Application Data

(62) Division of application No. 13/640,653, filed as application No. PCT/GB2011/000549 on Apr. 8, 2011, now Pat. No. 9,192,584.

(30) Foreign Application Priority Data

Apr. 12, 2010 (GB) .................................. 1006038.2

(51) Int. Cl.
| | | |
|---|---|---|
| A61K 9/10 | (2006.01) | |
| A61K 9/51 | (2006.01) | |
| A61K 31/536 | (2006.01) | |
| A61K 31/427 | (2006.01) | |
| A61K 31/513 | (2006.01) | |
| A61K 31/4725 | (2006.01) | |
| A61K 47/38 | (2006.01) | |
| A61K 47/10 | (2017.01) | |
| A61K 47/32 | (2006.01) | |

(52) U.S. Cl.
CPC .............. *A61K 9/10* (2013.01); *A61K 9/5123* (2013.01); *A61K 9/5138* (2013.01); *A61K 9/5146* (2013.01); *A61K 9/5161* (2013.01); *A61K 9/5192* (2013.01); *A61K 31/427* (2013.01); *A61K 31/4725* (2013.01); *A61K 31/513* (2013.01); *A61K 31/536* (2013.01); *A61K 47/10* (2013.01); *A61K 47/32* (2013.01); *A61K 47/38* (2013.01)

(58) Field of Classification Search
CPC .......... A61K 31/7056; A61K 47/48215; A61K 9/5123; A61K 9/5138; A61K 9/5146; A61K 9/5161; A61K 9/5192; A61K 9/1075; A61K 31/4725; A61K 31/427; A61K 31/513; A61K 31/536; A61K 47/10; A61K 47/28; A61K 47/32; C07H 19/056

See application file for complete search history.

(56) References Cited

U.S. PATENT DOCUMENTS

| | | | |
|---|---|---|---|
| 2007/0026056 A1* | 2/2007 | Rolf ...................... | A61F 13/023 424/449 |
| 2007/0207952 A1* | 9/2007 | Silva ................... | C07K 14/765 530/324 |
| 2013/0028946 A1 | 1/2013 | Foster et al. | |

FOREIGN PATENT DOCUMENTS

| | | |
|---|---|---|
| EP | 0872233 A1 | 10/1998 |
| GB | 2451811 A | 2/2009 |
| WO | 9635414 A1 | 11/1996 |
| WO | 03084462 A2 | 10/2003 |
| WO | 2004011537 A1 | 2/2004 |
| WO | 2005011636 A2 | 2/2005 |
| WO | 2006079409 A2 | 8/2006 |
| WO | 2007103294 A2 | 9/2007 |
| WO | 2008006712 A2 | 1/2008 |
| WO | 2008017867 A2 | 2/2008 |
| WO | 2009040818 A1 | 4/2009 |
| WO | 2010009146 A1 | 1/2010 |
| WO | 2010020518 A2 | 2/2010 |
| WO | 2010023066 A2 | 3/2010 |
| WO | WO 2010/023066 A2 * | 3/2010 |
| WO | 2010036211 A1 | 4/2010 |
| WO | 2010068899 A1 | 6/2010 |

OTHER PUBLICATIONS

United States Patent Office Final Rejection for U.S. Appl. No. 13/640,653 dated Apr. 1, 2015 (8 pages).
United States Patent Office Notice of Allowance for U.S. Appl. No. 13/640,653 dated Jun. 23, 2015 (9 pages).
Destache, C.J. et al., "Ritonavir-, Lopinavir-, and Efavirenz-containing nanoparticles: in vitro release of anti-retroviral therapy (ART)," 15th Conference on Retroviruses and Opportunistic Infections (EP-07) (Feb. 2008).
United Kingdom Patent Office Search Report for Application GB1006038.2 dated Aug. 6, 2010 (2 pages).

(Continued)

*Primary Examiner* — Blessing M Fubara
(74) *Attorney, Agent, or Firm* — Michael Best & Friedrich LLP

(57) ABSTRACT

The present invention provides a composition and an antiviral drug preparation, each comprising at least one water-insoluble antiviral drug and at least one water-soluble carrier material, wherein the water-insoluble antiviral drug is dispersed through the water-soluble carrier material in nano-disperse form. The present invention further provides processes for preparing the compositions and drug preparations, and also aqueous nano-dispersions obtained by combining water and the compositions.

18 Claims, 4 Drawing Sheets

(56) References Cited

OTHER PUBLICATIONS

M Fardis, R "5.20 Tenofovir Disoproxil Fumarate: A Oral Prodrug of Tenofovir", Prodrugs: Challenges and Rewards, Part 2, Editors: VJ Stella, RT Borchardt et al, Springer 2007 pp. 652 (pp. 648-657).
Van Eerdenbrugh et al: "Characterization of physico-chemical properties and pharmaceutical performance of sucrose co-freeze-dried solid nanoparticulate powders of the anti-HIV agent loviride prepared by media milling", International Journal of Pharmaceutics, Elsevier BV, NL, vol. 338, No. 1-2, May 23, 2007 (May 23, 2007), pp. 198-206, XP022093455, ISSN: 0378-5173, DOI: 10.1016/J. IJPHARM.2007.02.005, p. 199, col. 1, line 25-line 44, paragraphs [02.2], [02.4], [02.8], [2.12], paragraphs [03.2], [03.3] table 1, figure 7.
International Search Report and Written Opinion for corresponding International Application No. PCT/GB2011/000549 dated Mar. 13, 2012.
United States Office Action for U.S. Appl. No. 13/640,653 dated Mar. 25, 2014 (10 pages).
United States Office Action for U.S. Appl. No. 13/640,653 dated Aug. 6, 2014 (13 pages).
United States Patent Office Action for U.S. Appl. No. 13/640,653 dated Dec. 19, 2014 (7 pages).

* cited by examiner

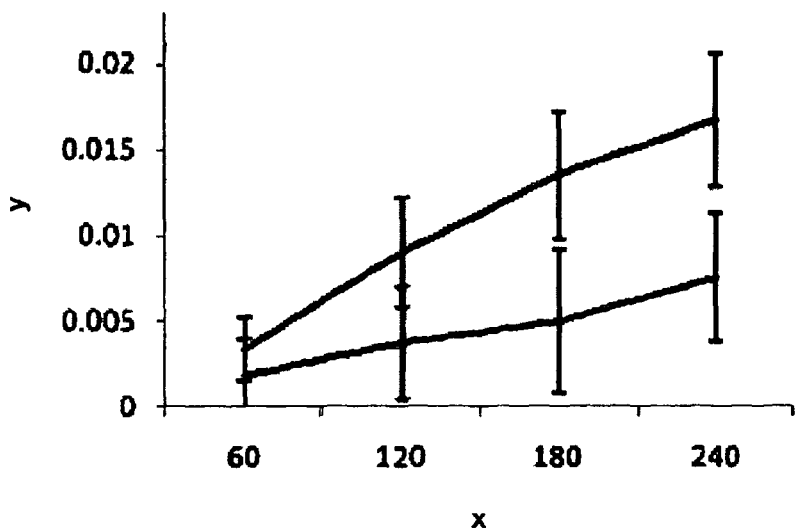
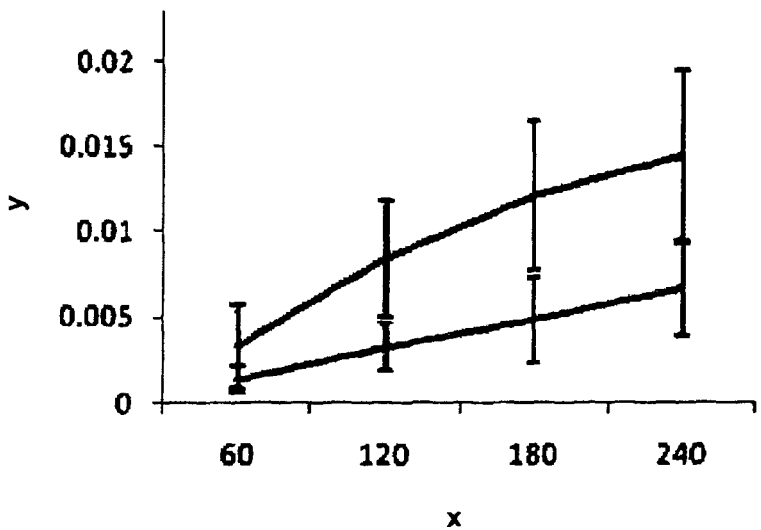

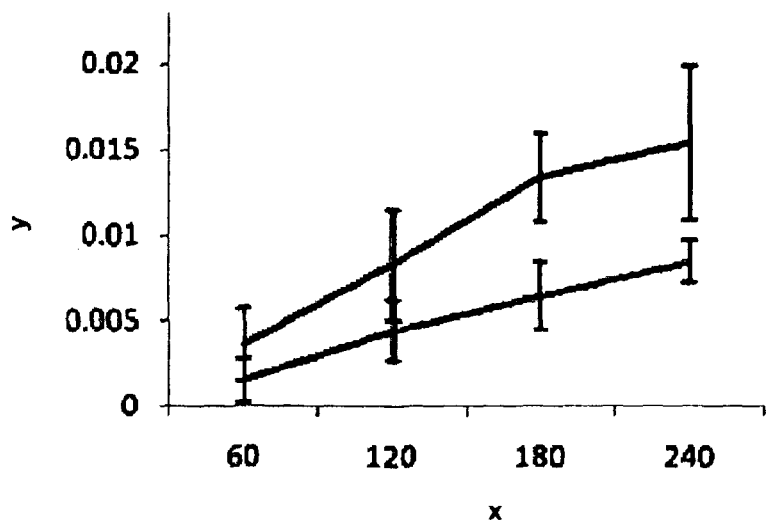
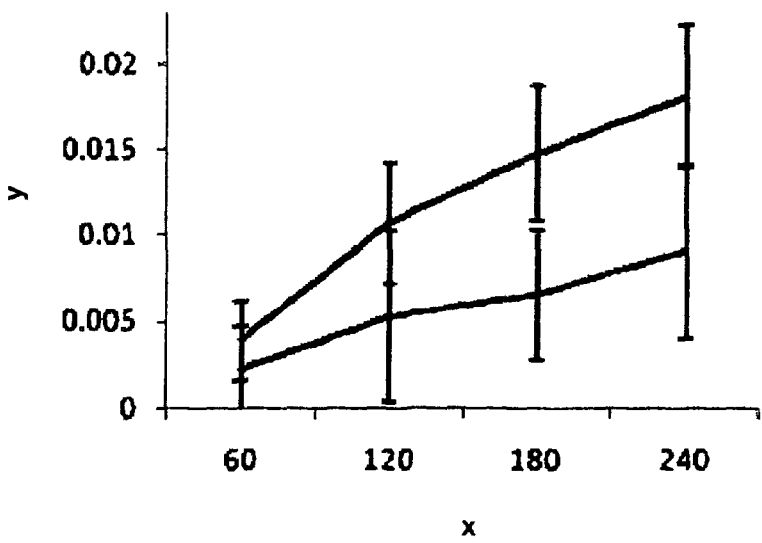

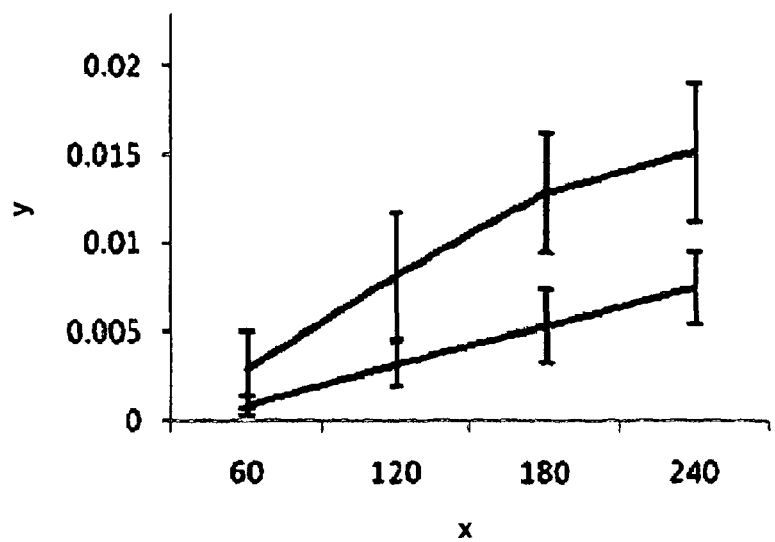
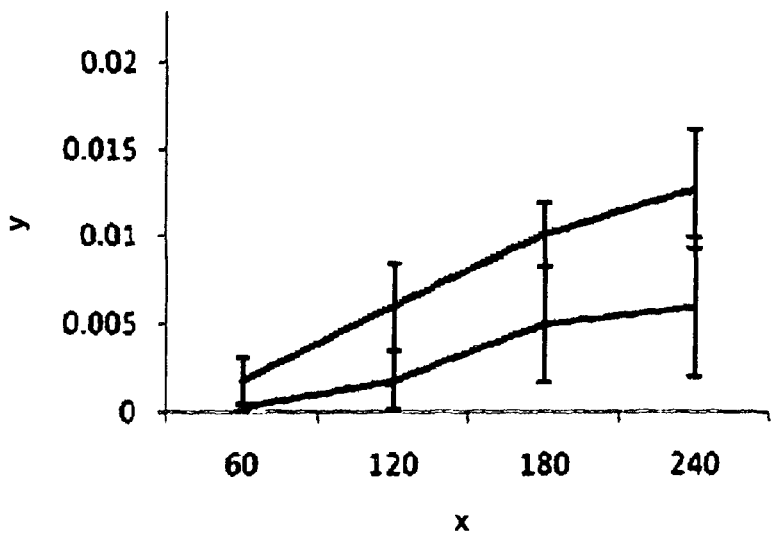

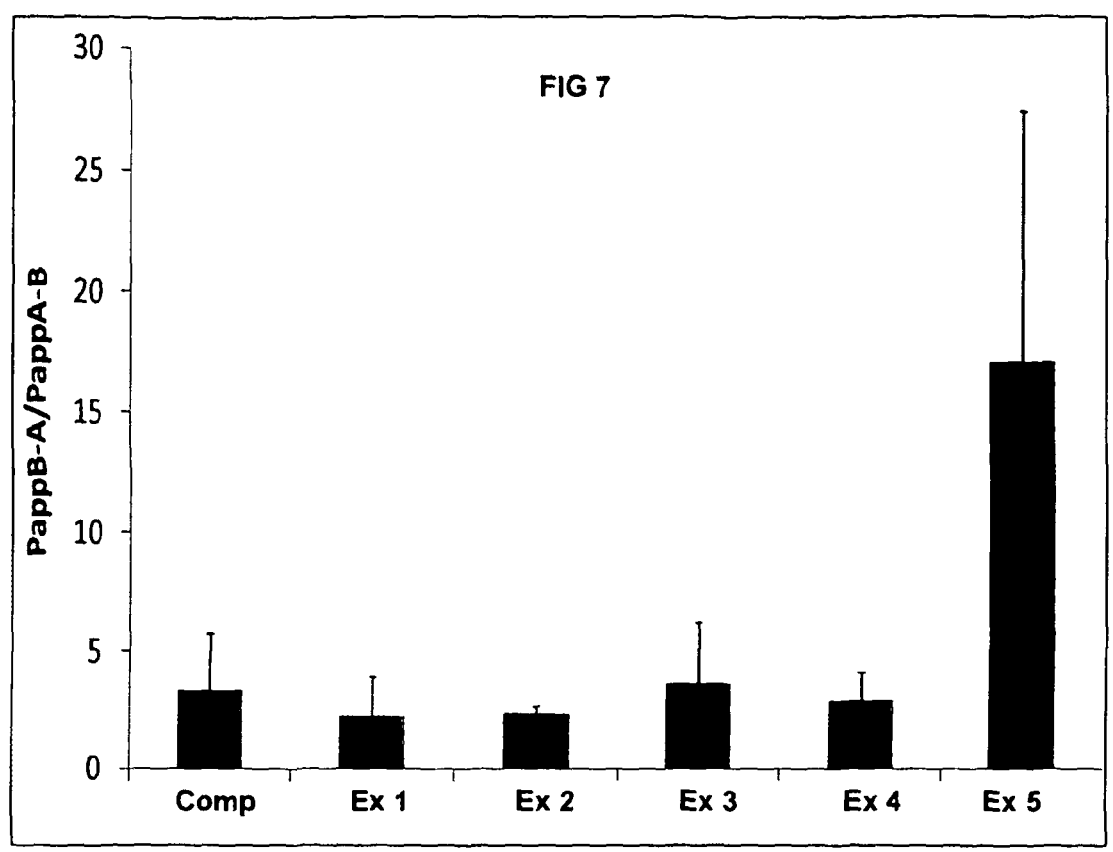

ANTIVIRAL COMPOSITIONS

CROSS-REFERENCE TO RELATED APPLICATIONS

This application is a divisional application of and claims priority to U.S. patent application Ser. No. 13/640,653, filed Oct. 11, 2012, which is a national phase application of PCT Application No. PCT/GB2011/000549, filed Apr. 8, 2011, which claims priority to United Kingdom Patent Application No. 1006038.2, filed Apr. 12, 2010, the entire contents of which are all hereby incorporated by reference herein.

BACKGROUND

The present invention relates to improvements in compositions comprising one or more antiviral drugs. In particular, the present invention relates to pharmaceutically-active compositions (and precursors thereof) which comprise a drug for treatment of infection caused by a virus, i.e. an antiviral drug. The present invention is especially (but not exclusively) concerned with compositions which comprise a drug for treatment of infection cause by a retrovirus, i.e. an antiretroviral drug.

The present invention further relates to a pharmaceutically-acceptable form of an antiviral drug, whether alone or in combination with another drug, such as another antiviral drug, or other pharmaceutically-acceptable excipients.

The present invention is believed to be generally applicable to compositions comprising any antiviral drug (i.e. for treating infection by viruses, such as the herpes virus, hepatitis B, hepatitis C, influenza, and the like), and especially those compositions comprising an antiretroviral drug (i.e. for treating infection by retroviruses), but will be described with particular reference to compositions comprising drugs for treating Human Immunodeficiency Virus (HIV) and Acquired Immune Deficiency Syndrome (AIDS).

SUMMARY

Retroviruses belong to the Retroviridae family of viruses. A retrovirus is a ribonucleic acid (RNA) virus that is replicated in a host cell via the reverse transcriptase enzyme to produce deoxyribonucleic acid (DNA) from its RNA genome. Normally, DNA would transcript into RNA, and RNA would translate into proteins. However, when a host cell is infected with a retrovirus, the transcription process is reversed, and the resultant DNA is then incorporated into the host's genome by an integrase enzyme. The virus thereafter replicates as part of the host cell's DNA.

Retroviruses are known to lead to certain types of cancers, such as leukaemia, in both humans and animals, as well as to a range of viral infections, including HIV, the virus that causes AIDS.

HIV and AIDS are diseases that are widespread, causing many deaths across the world annually. The estimated number of deaths from AIDS in 2008 was 2 million with the total number of people living with HIV/AIDS in the same year being 33.4 million. Over 25 million people are thought to have died of HIV/AIDS, and incidents of infection across the globe are estimated to be increasing, including in developed countries. Heterosexual transmission is now believed to have overtaken homosexual transmission and mother-to-child transmission is considered a major route for infection. Whilst drugs have been developed for the treatment of HIV and AIDS, as will be described in the following paragraph, there is a general and long-standing problem that the drugs have a poor water-solubility making their administration problematic and their bioavailability poor.

Antiviral drugs and medications have been developed and used to combat viruses and retroviruses; such drugs are known as "antiviral drugs" and "antiretroviral drugs" respectively. Classes of known antiretroviral drugs used in the treatment of HIV/AIDS include:

protease inhibitors (PIs), which target viral assembly by inhibiting the activity of protease, an enzyme involved in the HIV replication process;
  nucleoside reverse transcriptase inhibitors (NRTIs), nucleotide reverse transcriptase inhibitors (NtRTIs) and non-nucleoside reverse transcriptase inhibitors (NNRTIs), all of which inhibit the activity of the reverse transcriptase enzyme;
  integrase inhibitors, which are designed to block the action of integrase, a viral enzyme that insets the viral genome into the DNA of the host cell;
  entry inhibitors, also known as fusion inhibitors, which interfere with the binding, fusion and entry of HIV to a host cell;
  maturation inhibitors, which also inhibit the activity of protease.

Such antiviral and antiretroviral drugs are often given in combination and therefore technologies that are able to enhance activity, bioavailability and formulation scope (to produce combination drug formats) provide opportunities to enhance patient compliance and possibly reduce toxicity or drug-drug interactions.

HIV and AIDS drugs may be used in both the prevention and the treatment of the diseases. Patients in the advanced stages of AIDS may be unable to swallow tablets. Therefore it is desirable to have antiretroviral drugs available in liquid form to provide an injectable medication or to allow rectal administration. Liquid forms of medication also allow for a continuous variation in dosage and this is especially useful in the treatment of children, where dosage may be calculated on the basis of body weight.

There have been a number of prior art attempts to improve the aqueous solubility of different antiviral drugs, including antiretroviral drugs used in the treatment of HIV/AIDS.

WO03/084462 describes a process for manufacturing antiretroviral protease inhibitors having improved bioavailability by incorporation of piperine. The pharmaceutical compositions incorporating piperine may be prepared in the form of a liquid, powder, capsule, tablet or any other desired dosage form. Unfortunately this process is not compatible with all protease inhibitors, e.g. it does not work with ritonavir, and thus is limited because it is not generic.

EP0872233 describes pharmaceutical compositions of loviride whereby the dosage forms have a high drug content. These compositions comprise particles obtainable by melt-extruding a mixture comprising loviride and an appropriate water-soluble polymer and subsequently milling said melt-extruded mixture. Unfortunately the melt-extrusion process described is also non-generic because those antiretroviral drugs or other pharmaceutically acceptable excipients to be included within the final composition that exhibit any degree of thermal sensitivity are incompatible with this process.

Similarly, WO2008/017867 discusses the provision of an antiretroviral solid oral compositions manufactured using a melt extrusion process.

The prior art illustrates that there is indeed a need to provide otherwise water-insoluble antiretroviral drugs, and antiviral drugs more generally, in soluble form, and in such a manner as to provide physiologically-acceptable solutions. Furthermore it would be desirable to provide antiviral drugs and antiretroviral drugs that exhibit enhanced bioavailability compared to their currently available form.

The problem of water-insolubility of a particular species is not restricted to antiviral and antiretroviral drugs, and indeed in other fields, a number of technologies have been proposed to formulate an otherwise water-insoluble species.

For example, WO2004/011537 describes the formation of solid, porous beads comprising a three dimensional open-cell lattice of a water-soluble polymeric material. These are typically "emulsion-templated" materials formed by the removal of both water (the continuous, aqueous phase) and a non-aqueous dispersed (or discontinuous) phase from a high internal phase emulsion (HIPE), which has a water-soluble polymer dissolved in the continuous aqueous phase. The beads are formed by dropping the HIPE emulsion into a low temperature fluid, such as liquid nitrogen, followed by freeze-drying the particles formed in the low temperature fluid to remove the bulk of the continuous aqueous phase and the non-aqueous dispersed phase, to leave behind the polymer in the form of a 'skeletal' structure. The beads dissolve rapidly in water. Advantageously, a water-insoluble component dissolved in the non-aqueous phase of the emulsion prior to its freezing and drying disperses in water on dissolution of the polymer skeleton of the beads. At the priority date, and also at the filing date, it was not envisaged that the process described in WO2004/011537 would be suitable for application to antiviral drugs (including antiretroviral drugs), and as such there is no mention or suggestion of application of the invention therein to antiviral drugs.

WO2005/011636 discloses a non-emulsion based spray-drying process for forming 'solid amorphous dispersions' of drugs in polymers. In this method a polymer and a low-solubility drug are dissolved in a solvent and spray-dried to form dispersions, in which the drug is mostly present in an amorphous form rather than in a crystalline form.

WO2006/079409 and WO2008/006712 each describe how a water-insoluble material, which will form a nano-dispersion in water, can be prepared, preferably by a spray-drying process. In WO2006/079409, the water-insoluble materials are dissolved in the solvent-phase (i.e. the "oil" phase) of an emulsion, whilst a water-soluble structuring agent is dissolved in the aqueous phase of the emulsion. In WO2008/006712, the water-insoluble materials are dissolved in a single phase mixed solvent system and co-exist in the same phase as a water-soluble structuring agent. In both cases the liquid (i.e. the emulsion or the single phase mix of solvents) is dried above ambient temperature, such as by spray-drying, to produce powder particles of the structuring agent, as a carrier, with the water-insoluble materials dispersed therein. When these powder particles are placed in water, the water-soluble structuring agent dissolves to form a nano-dispersion of the water-insoluble material, with said nano-particles having a z-average particle size of typically below 300 nm in the water. The water-insoluble material behaves as though it were in solution.

WO2006/079409 shows that fluorescer materials prepared by the method disclosed exhibit better performance than those prepared by a known freeze-drying method.

WO2008/006712 makes it clear that a Triclosan™ nano-dispersion has the additional benefit that, weight for weight, it is more effective than is normally expected of Triclosan™ even at very low concentrations.

However, there is no disclosure or suggestion in any of these prior publications that the techniques disclosed therein would or could be applicable to antiviral drugs to effectively "solubilise" them.

Surprisingly, therefore, the present inventors have now determined that both the emulsion-based method and the single-phase method for producing particles which are capable of forming nano-dispersions of a water-insoluble material in water, as discussed above, can be used to produce a water-dispersible form of one or more antiviral drugs, including antiretroviral drugs, particularly of relatively water-insoluble antiretroviral drugs useful for treating HIV and AIDS.

BRIEF DESCRIPTION OF THE DRAWINGS

FIGS. 1-6 show the concentration of the drug (on the y-axis in micromoles) on the apical side (lower line) compared to the basolateral side (upper line) in the transwell over time (on the x-axis in minutes).

FIG. 7 is a graph showing the ratio of the apparent permeability from the apical side to the basolateral side ($P_{app}$A–B) compared to the apparent permeability from the basolateral side to the apical side ($P_{app}$B–A) that was calculated from the data obtained in Examples 1-5.

FIRST ASPECT

Accordingly, a first aspect of the present invention provides a composition comprising at least one water-insoluble antiviral drug and at least one water-soluble carrier material, wherein the water-insoluble antiviral drug is dispersed through the water-soluble carrier material in nano-disperse form.

The first aspect of the invention is especially applicable to water-insoluble antiretroviral drugs.

SECOND ASPECT

A second aspect of the present invention provides an antiviral drug preparation comprising at least one water-insoluble antiviral drug and at least one water-soluble carrier material, wherein the water-insoluble antiviral drug is dispersed through the water-soluble carrier material in nano-disperse form.

The second aspect of the invention is also especially applicable to water-insoluble antiretroviral drugs.

Particle Sizing

Throughout the specification, by a "nano-disperse" and like terms we mean a dispersion in which the z-average particle size (diameter), otherwise known as the hydrodynamic diameter, is less than 1000 nm. Preferably, the z-average diameter of the nano-disperse form of the water-insoluble antiviral drug is preferably below 800 nm, even more preferably below 500 nm, especially below 200 nm, and most especially below 100 nm. For example, the z-average diameter of the nano-disperse form of the water-insoluble antiviral drug may be in the range of from 50 to 750 nm.

The preferred method of particle sizing for the dispersed products of the present invention employs a Dynamic Light Scattering (DLS) instrument (Nano S, manufactured by Malvern Instruments UK). Specifically, the Malvern Instruments Nano S uses a red (633 nm) 4 mW Helium-Neon laser to illuminate a standard optical quality UV cuvette containing a suspension of the particles to be sized. The particle sizes quoted in this application are those obtained with that apparatus using the standard protocol provided by the instrument manufacturer. The size of the nano-particles in a dry solid material, such as the size of the water-insoluble antiviral drug nano-particles, are inferred from the measurement of the particle size subsequent to the dry solid material being dispersed in water.

It is believed that the particle size of the water-insoluble antiviral drug in the nano-dispersion brings many significant attendant advantages, including that a nano-dispersion with a smaller particle size is believed to be more stable than one with a larger particle size, that, upon dissolution of the carrier material in an aqueous medium, dispersion of the water-insoluble drug can occur extremely rapidly, preferably within 5 minutes of having been introduced into the aqueous medium.

The size of the particles means that water-clear dispersions can be achieved in some cases, i.e. the dispersed drug particles in an aqueous medium are invisible to the naked eye and the liquid appears clear.

Furthermore, there are a number of pharmacokinetic advantages associated with the nano-disperse scale of the products of the invention. It is believed that both the compositions and antiviral drug preparations according to the invention have increased bioavailability (i.e. an increased amount of the drug makes it into the bloodstream of a subject as a proportion of the amount swallowed, as compared to administration of the drug in known forms) which manifests as:

- an increased AUC, i.e. a greater total exposure to the drug over a 24-hour period;
- an increased C-max, i.e. a higher maximum concentration of the drug in the blood;
- an earlier C-max, i.e. the time taken for the maximum concentration of the drug in the bloodstream to be reached is reduced;
- an increased half-life of the drug, i.e. the length of time taken for the blood concentration of the drug to drop to 50% of its C-max; and
- decreased variability between fasted and non-fasted subjects.

Antiviral Drugs

As stated above, the antiviral drugs comprised in the compositions and drug preparations of the present invention are water-insoluble antiviral drugs. In the context of the present invention, "water-insoluble" as applied to the antiviral drug means that its solubility in water at ambient temperature and pressure is less than 10 g/L. For comparison, tenofovir disoproxil fumarate, which is an oral prodrug of tenofovir, has a high water solubility of 13.4 mg/ml (i.e. 13.4 g/L) according to M. Fardis and R. Oliyai of Gilead Sciences Inc. in their paper entitled: "5.20: Tenofovir Disoproxil Fumarate: An Oral Prodrug of Tenofovir"; page 652.

For the avoidance of any doubt, in the present application the term "ambient temperature" means 25° C. whilst "ambient pressure" means 1 atmosphere (101.325 kPa) of pressure.

Preferably, the water-insoluble antiviral drug has solubility in water at ambient temperature and pressure of less than 5 g/L, more preferably of less than 1 g/L, even more preferably of less than 150 mg/L, and especially of less than 100 mg/L. This solubility level provides the intended interpretation of what is meant by "water-insoluble" in the present specification.

Preferred water-insoluble antiviral drugs include those which treat infections caused by herpes viruses, hepatitis viruses, influenza viruses and retroviruses.

Preferred water-insoluble antiretroviral drugs include, but are not limited to, protease inhibitors (PIs), nucleoside reverse transcriptase inhibitors (NRTIs), nucleotide reverse transcriptase inhibitors (NtRTIs), non-nucleoside reverse transcriptase inhibitors (NNRTIs), integrase inhibitors, entry inhibitors, maturation inhibitors and pharmaceutically-acceptable salts and precursors thereof.

Advantageously the water-insoluble antiviral drugs may be one or more selected from:

- aciclovir, docosanol, edoxudine, famciclovir, foscarnet, idoxuridine, penciclovir, trifluridine, tromantidine, valaciclovir and vidarabine (all of which treat infection caused by one or more herpes viruses);
- adefovir, boceprevir, entecavir, ribavirin and taribavirin (all of which treat infection caused by one or more hepatitis viruses);
- amantadine, arbidol, oseltamivir, peramivir, rimantidine and zanamivir (all of which treat infection cause by one or more influenza viruses).

Advantageously the water-insoluble antiretroviral drug may be one or more selected from:

- amprenavir, atazanavir, darunavir, fosamprenavir, indinavir, lopinavir, nelfinavir, ritonavir, saquinavir and tipranavir (all of which are protease inhibitors);
- abacavir (ABC), amdoxovir, apricitabine (ATC), didanosine (ddI), elvucitabine, emtricitabine (FTC), entecavir (INN), lamivudine (3TC), racivir, stampidine, stavudine (d4T), zalcitabine (ddC) and zidovudine (AZT) (all of which are NRTIs);
- adefovir (also known as bis-POM PMPA) and tenofovir (both of which are NtRTIs);
- delavirdine, efavirenz, etravirine, lersivirine, loviride, nevirapine and rilpivirine (all of which are NNRTIs);
- elvitegravir, globoidnan A, GSK-572, MK-2048 and raltegravir (all of which are integrase inhibitors);
- enfuviritide, ibalizumab, maraviroc and vicriviroc (all of which are fusion/entry inhibitors);
- bevirimat and vivecon (both of which are maturation inhibitors);

and pharmaceutically-acceptable salts and precursors thereof, and mixtures thereof.

Any suitable pharmaceutically-acceptable salts of the antiviral drugs may be used, which salts would be well known to persons skilled in the art. Similarly, any suitable precursors of the antiviral drugs may be used, which precursors would be well known to persons skilled in the art. For example, suitable precursors may be in the form of pro-drugs, by which we mean a compound that is broken down in a subject to release the active antiviral drug.

Compositions and drug preparations according to the present invention may comprise mixtures of two or more antiviral drugs, pharmaceutically-acceptable salts and/or precursors thereof. Any such additional antiviral drug may be water-soluble (e.g. emtricitabine, which is an NRTI) and may be incorporated into a composition or drug preparation along with the water-soluble carrier material. Furthermore it may have surfactant properties. In the context of retrovirus infections, use of such mixtures of drugs is generally referred to as highly active antiretroviral therapy (HAART). The use of HAART is typical in the treatment of HIV and AIDS, as combinations of antiretroviral drugs are believed to create multiple obstacles to HIV replication and to improve treatment. Furthermore with HAART, the development of resistance to one or more of the drugs may be inhibited.

The compositions and drug preparations of the present invention are preferably substantially solvent-free. In the context of the present invention, the term "substantially solvent-free" means that the free solvent content of the compositions and drug preparations is less than 15%, preferably below 10%, more preferably below 5% and most preferably below 2%. For the avoidance of doubt, throughout this specification, all percentages are percentages by weight unless otherwise specified.

Carrier Material

As stated above, the carrier material comprised in the compositions and drug preparations of the present invention is a water-soluble carrier material. In the context of the present invention, "water-soluble" as applied to the carrier-material means that its solubility in water at ambient temperature and pressure is at least 10 g/L. The term "water-soluble" includes the formation of structured aqueous phases as well as true ionic solution of molecularly mono-disperse species. For comparison, ritonavir is poorly water-soluble having a solubility of 1 µg/ml (i.e. 0.001 g/L) at pH 6.8 and 37° C. according to J. Pharma. Sci., 2001, 90(8), 1015-25.

Preferred water-soluble carrier materials may be selected from one or more water-soluble inorganic materials, water-soluble surfactants, water-soluble polymers, water-soluble sugars and mixtures thereof, as discussed herein.

Polymeric Carrier Materials

Examples of suitable water-soluble polymeric carrier materials include:
(a) natural polymers (for example naturally occurring gums such as guar gum, alginate, locust bean gum or a polysaccharide such as dextran);
(b) cellulose derivatives for example xanthan gum, xyloglucan, cellulose acetate, methylcellulose, hydroxyethylcellulose, hydroxyethylmethylcellulose, hydroxypropylcellulose (HPC), hydroxypropylmethylcellulose (HPMC), carboxymethylcellulose and its salts (e.g. the sodium salt—SCMC), or carboxymethylhydroxyethylcellulose and its salts (e.g. the sodium salt);
(c) homopolymers of or copolymers prepared from two or more monomers selected from: vinyl alcohol, acrylic acid, methacrylic acid, acrylamide, methacrylamide, acrylamide methylpropane sulphonates, aminoalkylacrylates, aminoalkyl-methacrylates, hydroxyethylacrylate, hydroxyethylmethylacrylate, vinyl pyrrolidone, vinyl imidazole, vinyl amines, ethyleneglycol and other alkylene glycols, ethylene oxide and other alkylene oxides, ethyleneimine, styrenesulphonates, ethyleneglycolacrylates and ethyleneglycol methacrylate;
(d) cyclodextrins, for example beta-cyclodextrin;
(e) mixtures thereof.

For the avoidance of any doubt, it is acknowledged that some of the species identified above have both water-soluble and water-insoluble forms, e.g. cellulose acetate, the solubility of which is variable accordingly to its degree of substitution (DS) with acetyl groups. However, for the purposes of the present invention, it should be understood that only the water-soluble forms of any such species are to be considered.

When the polymeric material is a copolymer it may be a statistical copolymer (heretofore also known as a random copolymer), a block copolymer, a graft copolymer or a hyperbranched copolymer. Co-monomers other than those listed above may also be included in addition to those listed if their presence does not destroy the water-soluble or water dispersible nature of the resulting polymeric material.

Examples of suitable and preferred homopolymers include polyvinylalcohol (PVA), polyacrylic acid, polymethacrylic acid, polyacrylamides (such as poly-N-isopropylacrylamide), polymethacrylamide; polyacrylamines, polymethylacrylamines, (such as polydimethylaminoethylmethacrylate and poly-N-morpholinoethylmethacrylate), polyvinylpyrrolidone (PVP), polystyrenesulphonate, polyvinylimidazole, polyvinylpyridine, poly-2-ethyloxazoline polyethyleneimine and ethoxylated derivatives thereof.

In one aspect, polyethylene glycol (PEG), polyvinylpyrrolidone (PVP), poly(2-ethyl-2-oxazaline), polyvinyl alcohol (PVA), hydroxypropylcellulose (HPC) and hydroxypropylmethylcellulose (HPMC) and alginates are preferred polymeric carrier materials.

In another aspect, polyvinylpyrrolidone (PVP), polyvinyl alcohol (PVA), hydroxypropylcellulose (HPC) and hydroxypropylmethyl cellulose (HPMC) are preferred polymeric carrier materials.

For the avoidance of any doubt, if a polymeric carrier material is used in the present invention, it will be substantially without, and preferably completely free from, cross-linking because the purpose of the carrier material is to dissolve on contact with an aqueous medium. It is well known that cross-linking has a large effect on physical properties of a polymer because it restricts the relative mobility of the polymer chains, increases molecular weight and causes large scale network formation, thus preventing its dissolution capability. Polystyrene, for example, is soluble in many solvents such as benzene, toluene and carbon tetrachloride. Even with a small amount of cross-linking agent (divinylbenzene, 0.1%) however, the polymer no longer dissolves but only swells.

Surfactant Carrier Materials

Where the carrier material is a surfactant, the surfactant may be non-ionic, anionic, cationic, amphoteric or zwitterionic.

Examples of suitable non-ionic surfactants include ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; block copolymers of ethylene oxide and propylene oxide, i.e. poloxamers (available under the trade name Pluronics™); alkyl polyglucosides; stearol ethoxylates; alkyl polyglycosides.

Examples of suitable anionic surfactants include alkylether sulfates; alkylether carboxylates; alkylbenzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates.

Examples of suitable cationic surfactants include fatty amine salts; fatty diamine salts; quaternary ammonium compounds; phosphonium surfactants; sulfonium surfactants.

Examples of suitable zwitterionic surfactants include N-alkyl derivatives of amino acids (such as glycine, betaine, aminopropionic acid); imidazoline surfactants; amine oxides; amidobetaines.

Mixtures of surfactants may be used; in such mixtures there may be individual components which are liquid.

Alkoxylated non-ionic surfactants (especially poloxamers, e.g. Pluronic™ type materials), alkyl sulphonates, alkyl sulphates (especially sodium dodecyl sulphate (SDS)), sodium deoxycholate, sodium myristate, sodium docusate, ester surfactants (preferably esters of non-PEG-ylated sorbitan (so-called Span™ esters) and polysorbates, which are esters of PEG-ylated sorbitan (so-called Tween™ esters)) and cationic surfactants (especially cetyltrimethylammonium bromide—CTAB) are particularly preferred as surfactant carrier materials.

Inorganic Carrier Materials

The carrier material can also be a water-soluble inorganic material which is neither a surfactant nor a polymer. Simple organic salts have been found suitable, particularly in admixture with polymeric and/or surfactant carrier materials as described above. Suitable salts include carbonate, bicarbonates, halides, sulphates, nitrates and acetates, particularly soluble salts of sodium, potassium and magnesium. Preferred materials include sodium carbonate, sodium bicarbonate and sodium sulphate. These materials have the advantage that they are cheap and physiologically acceptable. They are also relatively inert as well as compatible with many materials found in pharmaceutical products.

Organic Carrier Materials

The carrier material can also be a water-soluble small organic material which is neither a surfactant, nor a polymer nor an inorganic carrier material. Simple organic sugars have been found to be suitable, particularly in admixture with a polymeric and/or surfactant carrier material as described above. Suitable small organic materials include mannitol, xylitol and inulin, etc.

Compositions and drug preparations according to the present invention may comprise two or more carrier materials. Mixtures of carrier materials are advantageous. Preferred mixtures include combinations of surfactants and polymer, for example which mixtures preferably include at least one of:
a) polyvinylalcohol (PVA), polyethylene glycol (PEG), polyvinylpyrrolidone (PVP), hydroxypropylcellulose and hydroxypropylmethyl cellulose (HPMC), alginates and, at least one of;

b) alkoxylated non-ionic surfactants (especially poloxamers, e.g. Pluronic™ type materials), alkyl sulphonates, alkyl sulphates (especially sodium dodecyl sulphate (SDS)), sodium deoxycholate, sodium myristate, sodium docusate, ester surfactants (preferably esters of non-PEG-ylated sorbitan (so-called Span™ esters) and polysorbates, which are esters of PEG-ylated sorbitan (so-called Tween™ esters) and cationic surfactants (especially cetyltrimethylammonium bromide—CTAB).

THIRD ASPECT

A third aspect of the present invention provides an aqueous nano-dispersion of at least one water-insoluble antiviral drug and at least one water-soluble carrier material, said nano-dispersion being obtained by combining water and the compositions or drug preparations described herein. On admixture of the compositions or drug preparations of the invention with an aqueous medium, such as water, the water-soluble carrier dissolves and the water-insoluble antiviral drug is dispersed, as nano-particles, through the aqueous medium in sufficiently fine form that it behaves like a soluble material in many respects.

The third aspect of the invention is especially applicable to water-insoluble antiretroviral drugs.

The particle size of the water-insoluble materials in the dry product is preferably such that, on dispersion in water the water-insoluble materials have a z-average particle size of less than 1000 nm as determined by the Malvern method described herein. It is believed that there is no significant reduction of nano-particle size for the antiviral drug on dispersion of the dry solid powder form in an aqueous medium.

Preferably, the z-average diameter of the nano-disperse form of the water-insoluble antiviral drug is less than 1000 nm, preferably below 800 nm, even more preferably below 500 nm, especially below 200 nm, and most especially below 100 nm. For example, the z-average diameter of the nano-disperse form of the water-insoluble antiviral drug may be in the range of from 50 to 750 nm. Z-average particle sizes as low as 74 nm have been measured in the Examples provided below.

The aqueous nano-dispersion may be prepared by any known method that the skilled person would deem suitable for combining a composition or a drug preparation according to the invention with an aqueous medium.

In relation to the nano-dispersions mentioned above, the preferred water-insoluble antiviral drugs and the preferred water-soluble carrier materials are as described above and as elaborated on in further detail below. Similarly the preferred physical characteristics of the nano-dispersion are as described above.

By applying the present invention significant levels of ‘water-insoluble’ materials can be brought into a state which is largely equivalent to true solution. When a liquid format pharmaceutical is required, the dry product may be dissolved in an aqueous medium so as to achieve a nano-dispersion comprising up to 5% (and preferably more than 0.1%, preferably more than 0.5% and more preferably more than 1%) of the water-insoluble material. Of course the skilled person will appreciate that the actual amount of water-insoluble material in the dispersion will ultimately depend on the manner in which the dispersion is to be administered, e.g. in an injectable form, as an oral liquid, in a form suitable for intravenous administration, for rectal administration, via an intranasal spray, etc.

It is envisaged that the aqueous nano-dispersion will be a form suitable for administration to a subject either ‘as is’ or following further dilution. In the alternative, the aqueous dispersion may be combined with other active materials to yield a medicament suitable for use in a combination therapy such as HAART.

FOURTH ASPECT

A fourth aspect of the present invention provides a process for preparing a composition comprising at least one water-insoluble antiviral drug and at least one water-soluble carrier material, wherein the water-insoluble antiviral drug is dispersed through the water-soluble carrier material in nano-disperse form, which process comprises the steps of:

(a) forming an emulsion comprising:
  (i) a solution of the water-insoluble antiviral drug in a water-immiscible solvent for the same, and
  (ii) a solution of the water-soluble carrier material in an aqueous solvent, and, (b) drying the emulsion to remove the aqueous solvent and the water-immiscible solvent to obtain a substantially solvent-free nano-dispersion of the antiviral drug in the carrier material.

For convenience, this type of method is referred to herein as the “emulsion” method. In this method, the water-insoluble drug may be dissolved in the water-immiscible, oily/organic solvent to form an oil phase, whilst the water-soluble carrier material may be dissolved in the aqueous solvent to form an aqueous phase. The emulsion may then be formed by combining the oil phase and the aqueous phase, in known manner, to form an oil-in-water (O/W) emulsion in which the oil phase is the internal/disperse/discontinuous phase and the aqueous phase is the external/continuous phase.

The fourth aspect of the invention is especially applicable to water-insoluble antiretroviral drugs.

Preferably, the non-aqueous (oil) phase comprises from about 10% to about 95% v/v of the emulsion, more preferably from about 20% to about 68% v/v. The aqueous solvent may be water.

The emulsions are typically prepared under conditions which are well known to those skilled in the art, for example, by using a magnetic stirring bar, a homogeniser, or a sonicator. The emulsions need not be particularly stable, provided that they do not undergo extensive phase separation prior to drying.

In a preferred method according to the invention, a water-continuous emulsion is prepared with an average dispersed-phase droplet size (using the Malvern peak intensity) of between 500 nm and 5000 nm. Sonication is also a particularly preferred way of reducing the droplet size for emulsion systems. We have found that a Heat Systems Sonicator XL operated at level 10 for two minutes is suitable.

FIFTH ASPECT

A fifth aspect of the present invention provides a process for preparing a composition comprising at least one water-insoluble antiviral drug and at least one water-soluble carrier material, wherein the water-insoluble antiviral drug is dispersed through the water-soluble carrier material in nano-disperse form, which process comprises the steps of:
(a) providing a solution comprising:
   (i) at least one non-aqueous solvent,
   (ii) optionally, an aqueous solvent,
   (iii) a water-soluble carrier material which is soluble in the mixture of (i) and (ii), and
   (iv) a water-insoluble antiviral drug which is soluble in the mixture of (i) and (ii), but not (ii) alone, and,
(b) drying the solution to remove the aqueous solvent (when present) and the non-aqueous solvent to obtain a substantially solvent-free nano-dispersion of the antiviral drug in the carrier material.

For convenience, this type of method is referred to herein as the "single-phase" method. Preferably, the mixture created is a single-phase solution. In this method, the water-insoluble drug and the water-soluble carrier material may both be dissolved in the (mixture of the) non-aqueous solvent (plus aqueous solvent) to form the single-phase solution.

The fifth aspect of the invention is especially applicable to water-insoluble antiretroviral drugs.

In the "single-phase" method according to the present invention, both the carrier material and the water-insoluble antiviral drug are soluble in a non-aqueous solvent or a mixture of such a solvent with an aqueous solvent. Both here and elsewhere in the specification the non-aqueous solvent can be a mixture of non-aqueous solvents. The aqueous solvent may be water.

In this case the feedstock of the drying step can be a single phase material in which both the water-soluble carrier material and the water-insoluble antiviral drug are dissolved. It is also possible for this feedstock to be an emulsion, provided that both the carrier and the agent are dissolved in the same phase.

Non-Aqueous Solvent

In preparing the compositions of the invention, a non-aqueous solvent is used, i.e. a volatile, non-aqueous solvent. This may either be a non-aqueous solvent that is miscible with the other solvents (optionally including an aqueous solvent) in pre-mix before drying or, a non-aqueous solvent that is water-immiscible and that together with an aqueous solvent may form an emulsion.

In one alternative form of the invention, a single, non-aqueous solvent is employed which can form a single phase with water in the presence of the antiviral drug, and the carrier material. Preferred solvents for these embodiments are polar, protic or aprotic solvents.

Particularly preferred non-aqueous solvents are selected from haloforms (preferably dichloromethane, chloroform), lower (C1-C10) alcohols (preferably methanol, ethanol, isopropanol, isobutanol), organic acids (preferably formic acid, acetic acid), amides (preferably formamide, N,N-dimethylformamide), nitriles (preferably acetonitrile), esters (preferably ethyl acetate) aldehydes and ketones (preferably methyl ethyl ketone, acetone), and water miscible species comprising heteroatoms (preferably tetrahydrofuran, dialkylsulphoxide). Of course the skilled person will appreciate that out of these, only water immiscible solvents are suitable for the "emulsion method" and as such can be appropriately selected.

Haloforms, lower alcohols, ketones and dialkylsulphoxides are the most preferred non-aqueous solvents.

In another alternative form of the invention the non-aqueous solvent is not miscible with an aqueous solvent and forms an emulsion.

The non-aqueous phase of the emulsion is preferably selected from one or more from the following group of volatile organic solvents:
alkanes, preferably heptane, n hexane, isooctane, dodecane, decane;
cyclic hydrocarbons, preferably toluene, xylene, cyclohexane;
halogenated alkanes, preferably dichloromethane, dichoroethane, trichloromethane (chloroform), fluorotrichloromethane and tetrachloroethane;
esters preferably ethyl acetate;
ketones preferably 2-butanone;
ethers preferably diethyl ether;
volatile cyclic silicones preferably either linear or cyclomethicones containing from 4 to 6 silicon units. Suitable examples include DC245 and DC345, both of which are available from Dow Corning Inc.

Preferred solvents include toluene, cyclohexane and ethyl acetate.

Preferred non-aqueous solvents, whether miscible or not, have a boiling point of less than 150° C. and, more preferably, have a boiling point of less than 100° C., so as to facilitate drying, particularly spray-drying under practical conditions and without use of specialised equipment. Preferably they are non-flammable, or have a flash point above the temperatures encountered in the processes of the invention.

Preferably, the non-aqueous solvent comprises from about 10% to about 95% v/v of any emulsion formed, more preferably from about 20% to about 80% v/v. In the single phase method the level of solvent is preferably 20-100% v/v.

Particularly preferred solvents are alcohols, particularly ethanol and halogenated solvents, more preferably chlorine-containing solvents, most preferably solvents selected from (di- or tri-chloromethane).

Co-Surfactant

In addition to the non-aqueous solvent, an optional co-surfactant may be employed in the composition prior to the drying step. The present inventors have determined that the addition of a relatively small quantity of a volatile co-surfactant reduces the particle diameter of the nano-disperse antiviral drug produced. This can have a significant impact on particle volume. For example, reduction from 297 nm to 252 nm corresponds to a particle size reduction of approximately 40%. Thus, the addition of a small quantity of co-surfactant offers a simple and inexpensive method for reducing the particle size of materials according to the present invention without changing the final product formulation.

Preferred co-surfactants are short chain alcohols or amine with a boiling point of less than 220° C.

Preferred co-surfactants are linear alcohols. Preferred co-surfactants are primary alcohols and amines. Particularly preferred co-surfactants are selected from the group consisting of the 3-6 carbon alcohols. Suitable alcohol co-surfactants include n-propanol, n-butanol, n-pentanol, n-hexanol, hexylamine and mixtures thereof.

Preferably the co-surfactant is present in a quantity (by volume) less than the solvent preferably the volume ratio between the solvent and the co-surfactant falls in the range 100:40 to 100:2, more preferably 100:30 to 100:5.

In the context of the present invention it is essential that both the carrier material and the antiviral drug are essentially fully dissolved in their respective solvents prior to the drying step, and preferably completely dissolved. It is not within the ambit of the present specification to teach the drying of slurries. For the avoidance of any doubt, it is therefore the case that the solids content of the emulsion or the mixture is such that over 90%, preferably over 95%, more preferably over 98%, and ideally 100% of the soluble material present is in solution prior to the drying step.

Drying

Preferably, the drying step simultaneously removes both the water and other solvents. The most preferred method for drying of the intermediate emulsion or solution is spray-drying. This is particularly effective at removing both the aqueous and non-aqueous volatile components to leave the carrier and antiviral drug behind in a powder form. Alternatively however drying may be accomplished by freeze-drying, which brings its own particular benefits, such as in the preparation of aseptic formulations for intravenous administration.

Spray-drying and freeze-drying are techniques well-known to those versed in the art.

For spray-drying, we have found that the B-290 Mini Spray Dryer available from Buchi is suitable for laboratory spray-drying. For large-scale spray-drying, a PHARMASD™ spray-dryer available from GEA Niro is suitable.

It is preferable that the drying temperature should be at or above 100° C., preferably above 120° C. and most preferably above 140° C. Elevated drying temperatures have been found to give smaller particles in the re-dissolved nanodisperse material. For freeze-drying, we have found that the VirTis bench-top BT4K ZL freeze drying apparatus is suitable for laboratory freeze-drying, whilst a Usifroid freeze-dryer available from Biopharma Process Systems Ltd is suitable for large-scale freeze-drying.

Drying Feedstocks

Typical feedstocks for either spray-drying or freeze-drying comprise:
 a) a surfactant,
 b) a non-aqueous solvent,
 c) more than 0.1% of at least one water-insoluble antiviral drug dissolved in the feedstock,
 d) a polymer, and,
 e) optional water.

Therefore, in the present invention, preferred feedstocks comprise:
 a) a surfactant selected from: a non-ionic poloxamer (especially a Pluronic™ material), alkyl sulphonates, alkyl sulphates (especially SDS), sodium deoxycholate, sodium mysristate, sodium docusate, ester surfactants (preferably Span™ and/or Tween™ sorbitan esters) and a cationic surfactant (especially cetyltrimethylammonium bromide—CTAB) and mixtures thereof,
 b) at least one non-aqueous solvent selected from dichloromethane, chloroform, ethanol, acetone, and mixtures thereof,
 c) more than 0.1% of at least one water-insoluble antiviral drug,
 d) a polymer selected from polyethylene glycol (PEG), polyvinylalcohol (PVA), polyvinylpyrrolidone (PVP), hydroxypropylcellulose (HPC) and hydroxypropylmethylcellulose (HPMC), alginates and mixtures thereof, and
 e) optionally an aqueous medium, especially water.

The drying feedstocks used in the present invention are either emulsions or solutions which preferably do not contain solid matter and in particular preferably do not contain any undissolved antiviral drug.

It is particularly preferable that the level of the antiviral drug in the composition should be such that the loading in the dried composition is greater than or equal to 30%, preferably greater than or equal to 40% and most preferably greater than or equal to 50%. Such compositions have the advantages of a small particle size and high effectiveness as discussed above.

The structure of the material obtained after the drying step is not well understood. It is believed that the resulting dry powder materials are not encapsulates, as discrete macroscopic bodies of the water-insoluble materials are not present in the dry product in a core-shell morphology. Neither are the dry materials 'dry emulsions' as little or none of the volatile solvent comprising the 'oil' phase of the emulsion remains after the drying step. On addition of water to the dry product the emulsion is not reformed, as it would be with a 'dry emulsion'. It is also believed that the compositions are not so-called solid solutions, as with the present invention the ratios of components present can be varied without loss of the benefits.

Preferably, the compositions produced after the drying step will comprise the antiviral drug and the carrier material in a weight ratio of from 1:500 to 85:15 (as antiviral drug:carrier material) to 1:100 to 85:15, and further preferably from 1:500 to 1:1 to 1:100 to 1:1. Typical levels of around 30 to 50% water-insoluble antiviral drug and 70 to 50% carrier material can be obtained by both spray-drying and freeze-drying.

In relation to the methods mentioned above, the preferred antiviral drugs and the preferred carrier materials are as described above and as elaborated on in further detail below. Similarly the preferred physical characteristics of the composition are as described above.

FURTHER ASPECTS

The products obtainable by the process aspects of the present invention are suitable for use in the preparation of medicaments for treatment or prophylaxis of viral diseases, including retroviral diseases, and particularly, where the antiviral drug is a water-insoluble antiretroviral drug, the preparation of medicaments for use in the treatment or prophylaxis of HIV and AIDS.

A sixth aspect of the present invention provides a method for the preparation of a medicament for use in the treatment of viral diseases, including retroviral diseases, which comprises the step of preparing a composition according to the present invention.

A seventh aspect of the present invention provides a composition as described herein for use in the treatment and/or prevention of a viral disease or condition, including a retroviral disease or condition (for example HIV and/or AIDS), in a subject.

An eighth aspect of the present invention provides the use of a composition as described herein in the manufacture of a medicament for use in treating and/or preventing a viral disorder or condition, including a retroviral disorder or condition, in a subject, for example for use in treating and/or preventing a retroviral disease or condition (for example HIV and/or AIDS) in a subject.

A ninth aspect of the present invention provides a method for treating and/or preventing a viral disorder or condition, including a retroviral disorder or condition (for example HIV and/or AIDS), in a subject in need thereof, which method comprises administering to said subject a therapeutically effective amount of a composition as described herein.

A tenth aspect of the present invention provides a kit for administering a water-insoluble antiviral drug to a subject comprising a composition as described herein.

The "subject" to which the composition of the invention may be administered is an animal, especially a warm-blooded animal, such as a domestic animal or man, particularly man.

For a better understanding, the present invention will now be more particularly described, by way of non-limiting example only.

EXAMPLES

Each of the following Examples was conducted at ambient temperature and pressure unless otherwise stated.

Preparation of Nano-Dispersions

Example 1

0.70 g of HPMC and 0.10 g of Pluronic™ F127 surfactant were dissolved into 30 ml of deionised water; 0.20 g of saquinavir mesylate was added into the aqueous solution following the addition of 30 ml of ethanol. A clear ethanol/water solution was obtained. The ethanol/water solution was spray-dried at 120° C. at a liquid feed rate of 2.5 ml/minute using a Buchi Mini B290 spray-dryer. A free flowing white powder containing 20 wt % saquinavir mesylate was obtained and collected.

The powder was dispersed into deionised water (5 mg/ml) for particle size analysis (Malvern Nano NS). The z-average particle size of saquinavir mesylate in this dispersion was 430±9 nm.

Example 2

0.70 g of HPC and 0.10 g of Pluronic™ F127 surfactant were dissolved into 30 ml of deionised water; 0.20 g of saquinavir mesylate was added into the aqueous solution following the addition of 30 ml of ethanol. A clear ethanol/water solution was obtained. The ethanol/water solution was spray-dried at 120° C. at a liquid feed rate of 2.5 ml/minute using a Buchi Mini B290 spray-dryer. A free flowing white powder containing 20 wt % saquinavir mesylate was obtained and collected.

The powder was dispersed into deionised water (5 mg/ml) for particle size analysis (Malvern Nano NS). The z-average particle size of saquinavir mesylate in this dispersion was 117±5 nm.

Example 3

0.70 g of PVP K30 and 0.10 g of Pluronic™ F127 surfactant were dissolved into 30 ml of deionised water; 0.20 g of saquinavir mesylate was added into the aqueous solution following the addition of 30 ml of ethanol. A clear ethanol/water solution was obtained. The ethanol/water solution was spray-dried at 120° C. at a liquid feed rate of 2.5 ml/minute using a Buchi Mini B290 spray-dryer. A free flowing white powder containing 20 wt % saquinavir mesylate was obtained and collected.

The powder was dispersed into deionised water (5 mg/ml) for particle size analysis (Malvern Nano NS). The z-average particle size of saquinavir mesylate in this dispersion was 74±8 nm.

Example 4

0.65 g of HPMC and 0.10 g of Pluronic™ F127 surfactant were dissolved into 30 ml of deionised water. 0.05 g of lecithin was dissolved into 40 ml of ethanol and 0.20 g of saquinavir mesylate was added into the aqueous solution following the addition of the 40 ml ethanol solution. A clear ethanol/water solution was obtained. The ethanol/water solution was spray-dried at 120° C. at a liquid feed rate of 2.5 ml/minute using a Buchi Mini B290 spray-dryer. A free flowing white powder containing 20 wt % saquinavir mesylate was obtained and collected.

The powder was dispersed into deionised water (5 mg/ml) for particle size analysis (Malvern Nano NS). The z-average particle size of saquinavir mesylate in this dispersion was 196±2 nm.

Example 5

0.65 g of PVA and 0.10 g of Pluronic™ F127 surfactant were dissolved into 30 ml of deionised water. 0.05 g of Span 80 was dissolved into 30 ml of ethanol and 0.20 g of saquinavir mesylate was added into the aqueous solution following the addition of the 30 ml ethanol solution. A clear ethanol/water solution was obtained. The ethanol/water solution was sprayed dried at 120° C. at a liquid feed rate of 2.5 ml/minute using a Buchi Mini B290 spray-dryer. A free flowing white powder containing 20 wt % saquinavir mesylate was obtained and collected.

The powder was dispersed into deionised water (5 mg/ml) for particle size analysis (Malvern Nano NS). The z-average particle size of saquinavir mesylate in this dispersion was 336±7 nm.

A summary of the nano-dispersions prepared in Examples 1 to 5 above is shown in Table I below.

TABLE I

| | Example | | | | |
|---|---|---|---|---|---|
| | 1 | 2 | 3 | 4 | 5 |
| % Saquinavir Mesylate | 20 | 20 | 20 | 20 | 20 |
| % HPMC | 70 | 0 | 0 | 65 | 0 |
| % PVP | 0 | 0 | 70 | 0 | 0 |
| % HPC | 0 | 70 | 0 | 0 | 0 |
| % PVA | 0 | 0 | 0 | 0 | 65 |
| % Pluronic ™ F127 | 10 | 10 | 10 | 10 | 10 |
| % Lecithin S75 | 0 | 0 | 0 | 5 | 0 |
| % Span 80 | 0 | 0 | 0 | 0 | 5 |
| z-average particle size (nm) | 430 | 117 | 74 | 196 | 336 |

The five nano-dispersions of Examples 1 to 5 were assessed for their permeability across Caco-2 cell monolayers in order to determine the effects on transcellular passage, as will be described in more detail below.

In Vitro Intestinal Permeation Model

Caco-2 cells were cultured in Dulbecco's modified Eagle's medium and maintained at 37° C. in a 10% $CO_2$ incubator. Following confluence, the cells were split using 0.25% trypsin-EDTA, plated onto polycarbonate membrane transwells (0.4 μm, 4.7 cm² growth area, 24 mm insert diameter) at a density of 0.5×106 cells/cm². The medium was then changed every 2 to 3 days and the cells used for transport experiments between 14 and 21 days post-seeding. Prior to experimentation, transepithelial electrical resistance (TER) across the cell monolayers was monitored using a Millicell-ERS (electrical resistance system) to assess cell monolayer integrity.

The cell monolayers were then equilibrated in warm (37° C.) transport medium (Hanks, balanced salt solution containing 10 mM HEPES and buffered to pH 7.4 with sodium hydroxide). The medium in the apical (for apical to basolateral transport) or basolateral (for basolateral to apical transport) chamber was removed and replaced with an equal volume of pre-warmed transport medium containing either nanoparticulate or unmodified saquinavir. At 30, 60, 90, 120 and 150 minutes, 100 μl samples were taken from the receiver chamber and analysed using HPLC MS/MS. Finally, the integrity of the monolayer was re-assessed using radio-labelled mannitol, which is known not to pass through intact monolayers.

The apparent permeability coefficient ($P_{app}$ (cm s$^{-1}$)) was determined from the amount of compound transported per time. $P_{app}$ was calculated according to the following equation:

$$P_{app} = (dQ/dt) \cdot (1/(AC_0))$$

where:
(dQ/dt) is the steady-state flux (mmol s$^{-1}$)
A is the surface area of the filter (cm²)
$C_0$ is the initial concentration in the donor chamber (mM).

FIGS. 1 to 6 show the concentration of the drug (on the y-axis in micromoles) on the apical side (lower line) compared to the basolateral side (upper line) in the transwell over time (on the x-axis in minutes).

FIG. 1 shows the data obtained when saquinavir is dissolved into DMSO, as a comparative example, and FIGS. 2 to 6 show the data obtained when saquinavir is prepared in nano-disperse form according to Examples 1 to 5 respectively. Thus FIGS. 1 to 6 show that the transport of saquinavir in nano-particulate form is effectively the same as the transport of molecularly dissolved saquinavir in DMSO.

The ratio of the apparent permeability from the apical side to the basolateral side ($P_{app}$A–B) compared to the apparent permeability from the basolateral side to the apical side ($P_{app}$B–A) was calculated from the data obtained and shown in FIG. 7. If this ratio is less than 1 then transport of the drug from the gut to the bloodstream is poor. Ideally a ratio of greater than 1 indicates successful transport of the drug to the bloodstream; if this is a large number then there is good transport.

For most of the compositions (i.e. Examples 1 to 4), the basolateral transport appears to be the same as for that of normal 'dissolved' saquinavir (i.e. the comparative example). Therefore, the nano-disperse particulate formulations in Examples 1 to 4 all behave similarly to non-dispersed saquinavir dissolved in DMSO. For the formulation of Example 5, the basolateral transport appeared to be less than that of normal saquinavir (as shown by the higher ratio). However, quantitatively, this change equates to at least a 6-fold increase in apparent permeability for Example 5 and it indicates that the nanodispersed saquinavir of Example 5 is somehow bypassing efflux from the apical membrane.

Example 6

1 mg of efavirenz was dissolved in 0.1 ml of chloroform; 3 mg of Brij-58 surfactant and 6 mg polyvinylpyrrolidone were dissolved in 0.4 ml of water. Each of these solutions were combined and emulsified using a UP400S sonicator (20% power setting; 100% duty cycle for 7 seconds). The resulting emulsion was frozen in liquid nitrogen and freeze-dried over 48 hours at a constant pressure of 40 microbar using a Virtis Benchtop freeze-drier.

1 ml of water was added to the resultant powder, and the resulting dispersion analysed for particle size using DLS (Malvern Nano NS). The z-average particle size of efavirenz in this dispersion was 240 nm.

Example 7

1 mg of lopinavir was dissolved in 0.1 ml of chloroform; 3 mg of sodium docusate surfactant and 6 mg hydroxypropylcellulose were dissolved in 0.4 ml of water. Each of these solutions were combined and emulsified using a UP400S sonicator (20% power setting; 100% duty cycle for 7 seconds). The resulting emulsion was frozen in liquid nitrogen and freeze-dried over 48 hours at a constant pressure of 40 microbar using a Virtis benchtop freeze-drier.

1 ml of water was added to the resultant powder, and the resulting dispersion analysed for particle size using DLS (Malvern Nano NS). The z-average particle size of efavirenz in this dispersion was 423 nm.

Example 8

1 mg of ritonavir was dissolved in 0.1 ml of chloroform; 3 mg of Tween-80™ surfactant and 6 mg polyvinylalcohol were dissolved in 0.4 ml of water. Each of these solutions were combined and emulsified using a UP400S sonicator (20% power setting; 100% duty cycle for 7 seconds). The resulting emulsion was frozen in liquid nitrogen and freeze-dried over 48 hours at a constant pressure of 40 microbar using a Virtis benchtop freeze-drier.

1 ml of water was added to the resultant powder, and the resulting dispersion analysed for particle size using DLS (Malvern Nano NS). The z-average particle size of efavirenz in this dispersion was 326 nm.

The invention claimed is:

1. A substantially solvent-free composition consisting of at least one water-insoluble antiviral drug and at least one water-soluble carrier material, said water-soluble carrier material being selected from the group consisting of water-soluble inorganic materials, water-soluble surfactants, water-soluble polymers, water-soluble sugars and mixtures thereof, wherein the water-insoluble antiviral drug is dispersed through the water-soluble carrier material in nano-disperse form, said composition being obtained by a process comprising:
   (a1) forming an emulsion comprising:
      (i) a solution of the water-insoluble antiviral drug in a water-immiscible solvent, and
      (ii) a solution of the water-soluble carrier material in an aqueous solvent, or
   (a2) providing a single-phase solution comprising:
      (iii) at least one non-aqueous solvent,
      (iv) an aqueous solvent,
      (v) a water-soluble carrier material dissolved in the mixture of (iii) and (iv), and
      (vi) a water-insoluble antiviral drug dissolved in the mixture of (iii) and (iv), but not (iv) alone, and,
   (b) spray-drying or freeze-drying the emulsion or single-phase solution to remove the aqueous solvent and the water-immiscible solvent to obtain the substantially solvent-free composition comprising a nano-dispersion of the antiviral drug in the carrier material,
   and wherein the water-insoluble antiviral drug does not comprise darunavir.

2. The substantially solvent-free composition as claimed in claim 1, wherein the z-average particle size of the nano-disperse form of the water-insoluble antiviral drug is below 1000 nm.

3. The substantially solvent-free composition as claimed in claim 1, wherein the water-insoluble antiviral drug has a water solubility of less than 10 g/L.

4. A substantially solvent-free composition as claimed in claim 1 wherein the antiviral drug is selected from the group consisting of: aciclovir, docosanol, edoxudine, famciclovir, foscarnet, idoxuridine, penciclovir, trifluridine, tromantidine, valaciclovir, vidarabine, adefovir, entecavir, ribavirin, taribavirin, amantadine, arbidol, oseltamivir, peramivir, rimantidine, zanamivir, and mixtures thereof.

5. A substantially solvent-free composition as claimed in claim 1 comprising a mixture of two or more antiviral drugs, pharmaceutically-acceptable salts or precursors thereof.

6. A substantially solvent-free composition as claimed in claim 1, wherein the non-aqueous solvent is selected from the group consisting of chloroform, toluene, cyclohexane, ethyl acetate, dichloromethane, and mixtures thereof.

7. A substantially solvent-free composition as claimed in claim 1, wherein the water-soluble polymeric carrier material is selected from the group consisting of polyvinylalcohol, polyethylene glycol, polyvinylpyrrolidone, poly(2-ethyl-2-oxazaline), hydroxypropylcellulose, hydroxypropylmethylcellulose, alginates, and mixtures thereof.

8. A substantially solvent-free composition as claimed in claim 1, wherein the surfactant is selected from the group consisting of alkoxylated non-ionic surfactant, ether sulfate surfactant, cationic surfactant, ester surfactant, and mixtures thereof.

9. An aqueous nano-dispersion of at least one water-insoluble antiviral drug and at least one water-soluble carrier material obtained by combining water and a composition as claimed in claim 1.

10. An aqueous nano-dispersion as claimed in claim 9, wherein the nano-disperse form of the water-insoluble antiviral drug has a z-average particle size of below 1000 nm.

11. The substantially solvent-free composition as claimed in claim 1, wherein the antiviral drug is selected from the group consisting of: protease inhibitors, nucleoside/nucleotide reverse transcriptase inhibitors, non-nucleoside reverse transcriptase inhibitors, integrase inhibitors, entry inhibitors, maturation inhibitors, pharmaceutically-acceptable salts thereof, and mixtures thereof.

12. The substantially solvent-free composition as claimed in claim 11, wherein the protease inhibitor is selected from the group consisting of: amprenavir, atazanavir, boceprevir, fosamprenavir, indinavir, lopinavir, nelfinavir, ritonavir, saquinavir, tipranavir, and mixtures thereof.

13. The substantially solvent-free composition as claimed in claim 11, wherein the nucleoside/nucleotide reverse transcriptase inhibitor is selected from the group consisting of: abacavir, adefovir, amdoxovir, apricitabine, didanosine, elvucitabine, emtricitabine, entecavir, lamivudine, racivir, stampidine, stavudine, tenofovir, zalcitabine, zidovudine, and mixtures thereof.

14. The substantially solvent-free composition as claimed in claim 11, wherein the nucleotide/nucleotide reverse transcriptase inhibitor is selected from the group consisting of: adefovir, tenofovir, and mixtures thereof.

15. A substantially solvent-free composition as claimed in claim 11, wherein the non-nucleoside reverse transcriptase inhibitor is selected from the group consisting of: delavirdine, efavirenz, etravirine, lersivirine, loviride, nevirapine, rilpivirine, and mixtures thereof.

16. A substantially solvent-free composition as claimed in claim 11, wherein the antiviral drug is an integrase inhibitor selected from the group consisting of: elvitegravir, globoidnan A, GSK-572, MK-2048, raltegravir, and mixtures thereof.

17. A substantially solvent-free composition as claimed in claim 11, wherein the antiviral drug is an entry inhibitor selected from the group consisting of: enfuviritide, ibalizumab, maraviroc, vicriviroc, and mixtures thereof.

18. A substantially solvent-free composition as claimed in claim 11, wherein the antiviral drug is a maturation inhibitor selected from the group consisting of: bevirimat, vivecon, and mixtures thereof.

* * * * *